United States Patent
Sloan et al.

[19]

[11] Patent Number: 5,850,940
[45] Date of Patent: Dec. 22, 1998

[54] HAND-HOLDABLE, REUSEABLE CONTAINERS HAVING ANIMAL CONFIGURATIONS

[76] Inventors: Mark A. Sloan; Jack C. Sloan, both of 2552 E. Alameda, Unit 118, Denver, Colo. 80209; Deanna J. Nervig, 201 Rushmore, Elizabeth, Colo. 80107

[21] Appl. No.: 729,509

[22] Filed: Oct. 15, 1996

[51] Int. Cl.$^6$ .................................................. B65D 37/00
[52] U.S. Cl. ...................... 222/78; 222/212; 222/214; 222/482; 222/514.5; 222/541.6; 222/192
[58] Field of Search ..................... 99/36, 40; 222/78, 222/482, 541.5, 541.6, 212, 192, 214

[56] References Cited

U.S. PATENT DOCUMENTS

| | | | |
|---|---|---|---|
| D. 169,309 | 4/1953 | Fuller | D99/40 |
| D. 176,104 | 11/1955 | Brooks | D99/40 |
| D. 347,573 | 6/1994 | Bishop | D99/40 |
| 1,327,190 | 1/1920 | Bigoney | 222/541.6 |
| 2,689,668 | 9/1954 | Hexel | 222/131 |
| 3,105,612 | 10/1963 | Krasnoff et al. | 222/78 |
| 3,474,933 | 10/1969 | Malpas | 222/554 X |
| 4,073,397 | 2/1978 | Snodgrass | 215/1 |
| 4,593,817 | 6/1986 | Ferrero | 206/457 |
| 4,749,104 | 6/1988 | Chao | 222/78 |
| 4,781,314 | 11/1988 | Schoonover et al. | 222/482 X |
| 5,228,595 | 7/1993 | Booker | 222/78 |
| 5,472,112 | 12/1995 | Maciejewski | 222/541.6 X |
| 5,489,050 | 2/1996 | Finkiewicz et al. | 222/78 X |

FOREIGN PATENT DOCUMENTS 272699  6/1927  United Kingdom ..................... 222/78

*Primary Examiner*—Kenneth Bomberg
*Attorney, Agent, or Firm*—Dorr, Carson, Sloan & Birney, P.C.

[57] ABSTRACT

Hand-holdable containers for various, liquid, powder and solid products can be made suitable for a "second use" by provided such containers with an animal simulating configuration, a head (cap) which is attached to the animal's neck region, a first opening in the animal's neck region for dispensing the original product stored in the container and a sealed second opening that can be readily unsealed when the original product stored in the container is used up so that said container can be used to store or display other items.

7 Claims, 6 Drawing Sheets

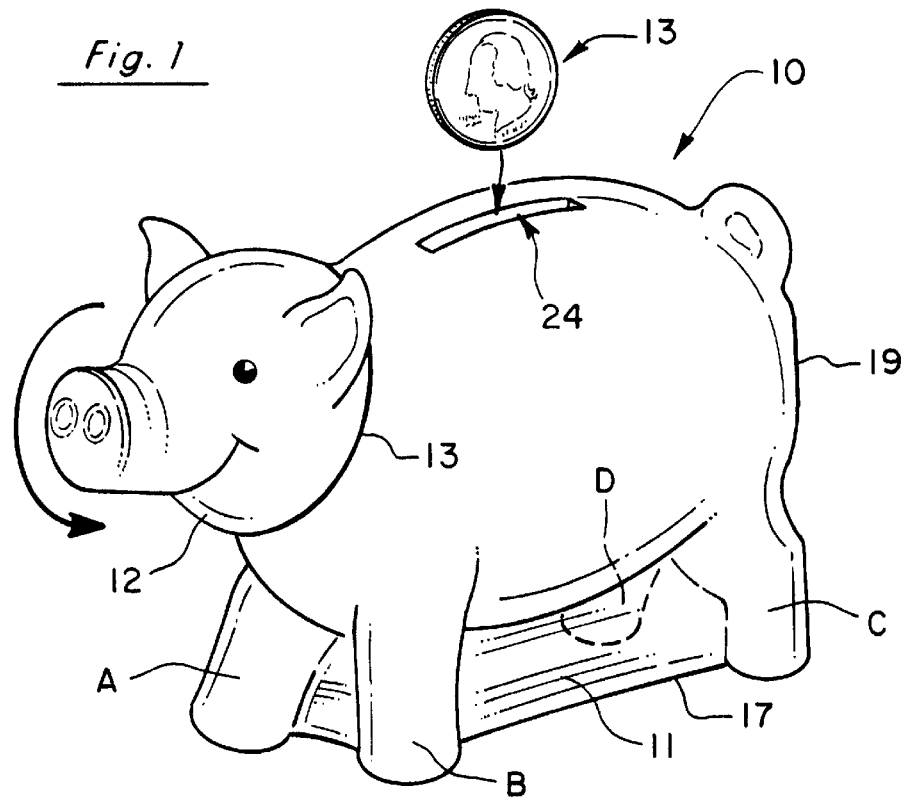
Fig. 1
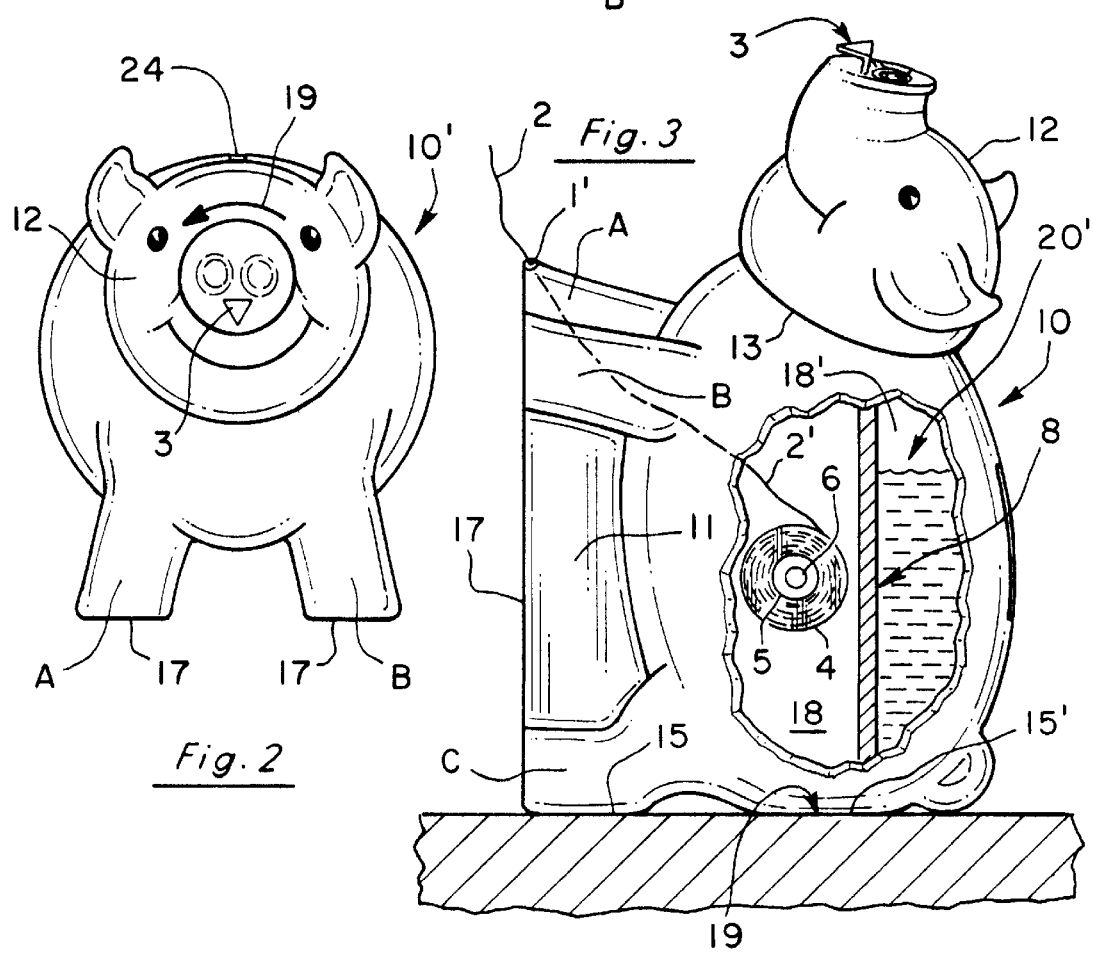
Fig. 2
Fig. 3

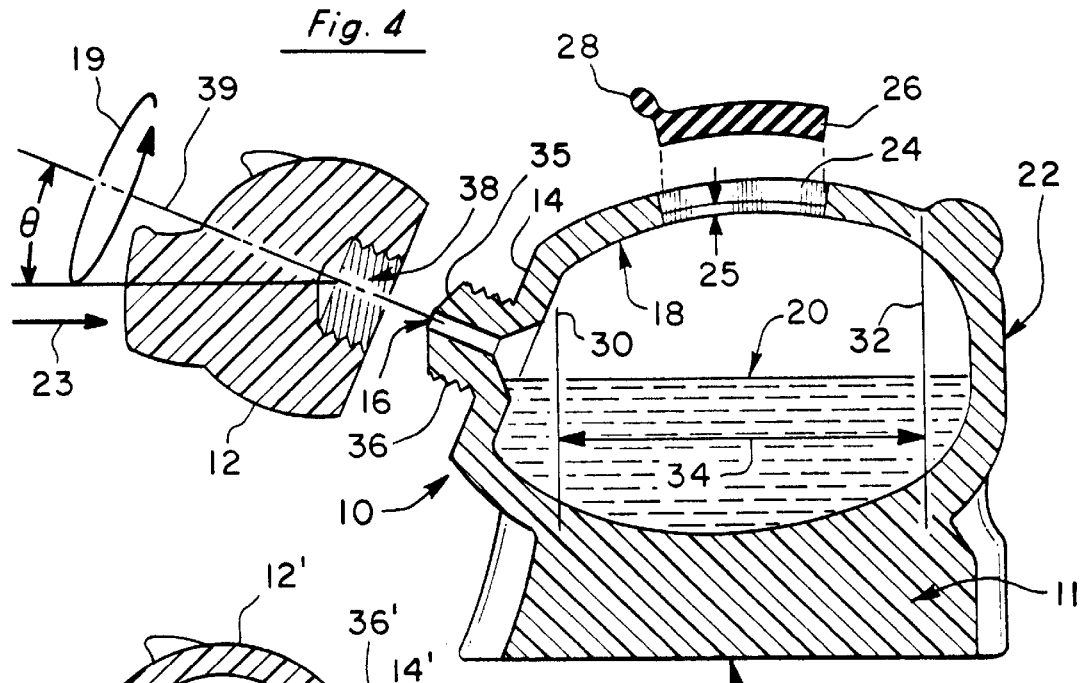
Fig. 4
Fig. 4(a)
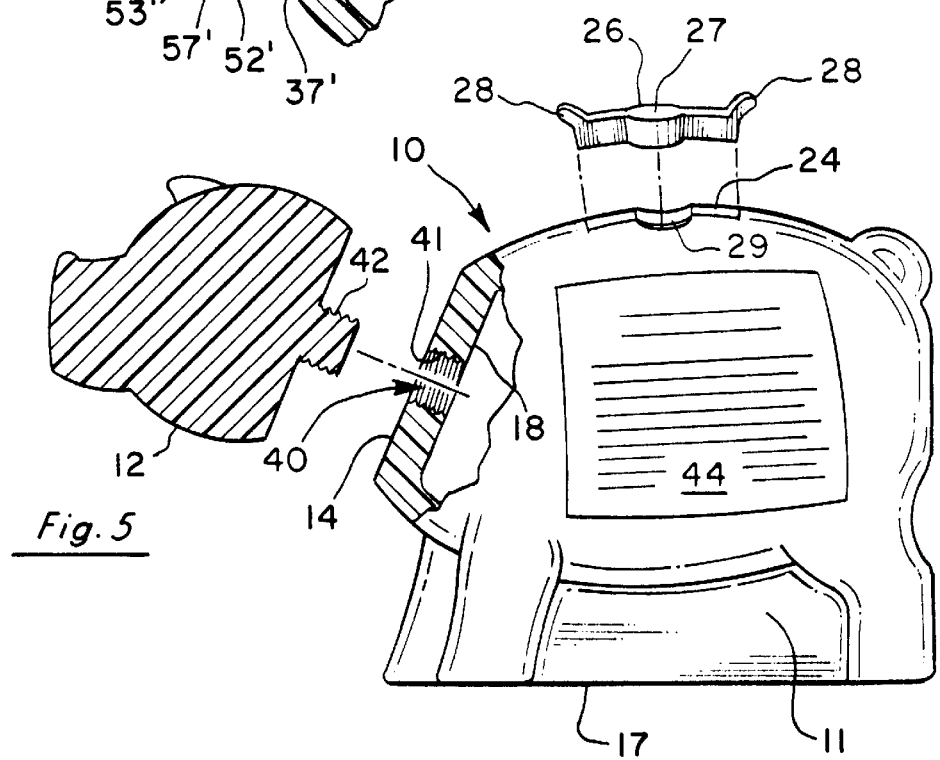
Fig. 5

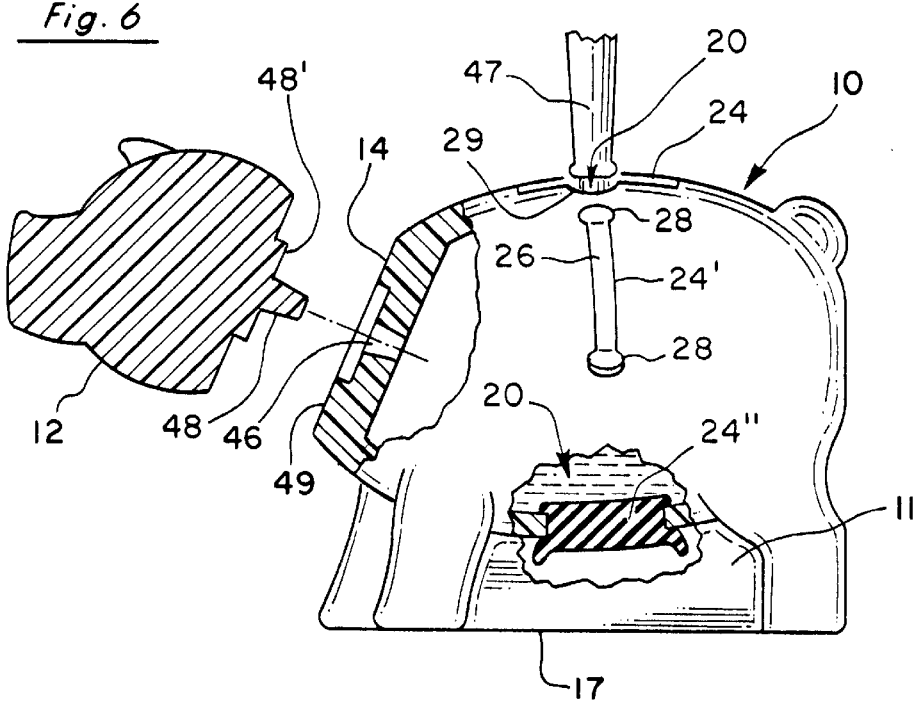
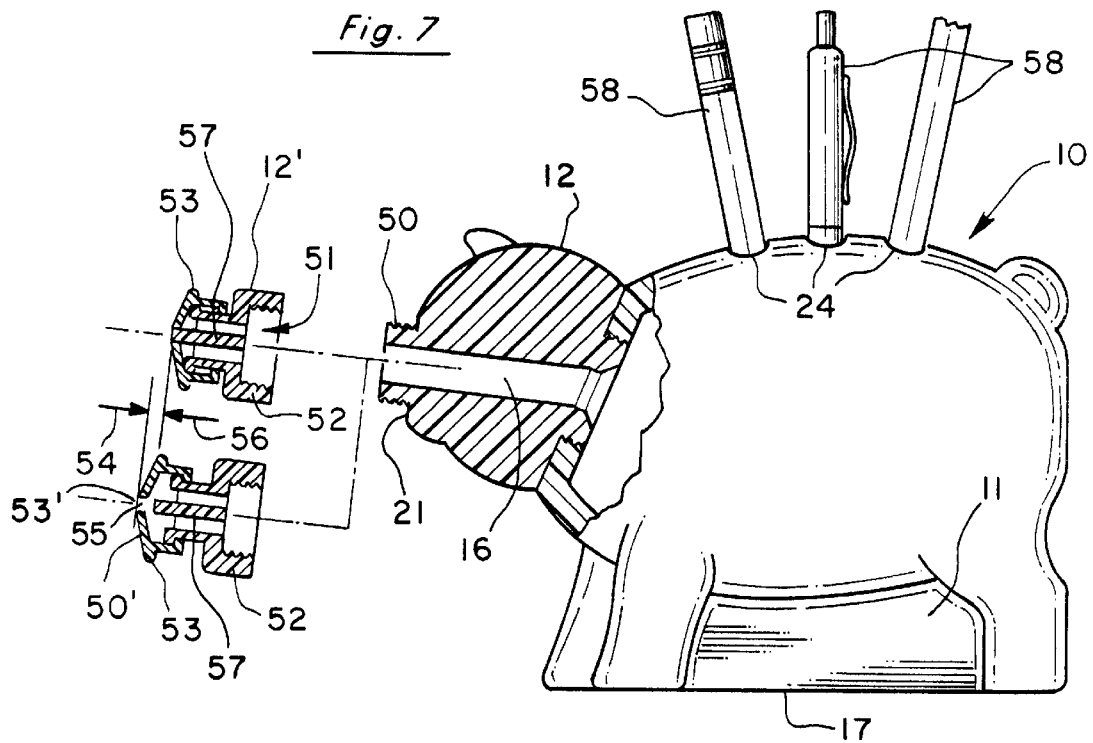

HAND-HOLDABLE, REUSEABLE CONTAINERS HAVING ANIMAL CONFIGURATIONS

BACKGROUND OF THE INVENTION

1. Field of the Invention

This invention generally relates to hand-holdable containers for products that normally are dispensed from the container into the user's hand or mouth (e.g., various liquid products such as after-shave lotion, hair tonic, hand lotion, liquid soap, cologne, beverages, mouthwash, etc.; various solid products such as vitamin pills, hard candy, dental floss, etc.; and various powdered products such as talc, spices, soap powder, etc.). More particularly, this invention is concerned with "novelty" type containers for such products, and especially those novelty containers simulating at least some of the anatomical features of an animal.

2. Statement of the Problem

Most hand-holdable containers are immediately thrown away after the product contained therein has been used up. This probably follows from the fact that most containers of this kind are, at best, made with visually distinctive configurations in order to help identify and "sell" the product originally contained therein—but such containers seem to have very little or no "secondary" appeal and/or utility. This circumstance has been recognized in some limited cases, but has not been fully addressed by prior art novelty containers, and especially those relatively small novelty containers used to dispense products into their user's hand or mouth.

For example, U.S. Pat. No. 4,073,397 discloses a container generally having the shape of a duck. The liquid contents of the duck-shaped container are dispensed from a threaded spout in the beak or neck region of the duck's anatomy. The beak or head serves as the cap of the container. After the contents of this container have been used up, it is especially well suited for use as a duck decoy, or as a child's toy.

U.S. Pat. No. 4,749,104 discloses a cleansing liquid dispenser that is provided with suction cups for mounting said dispenser to a tile wall. The top of the dispenser has a nose piece that is compression fitted on to a rocket-configured body. When the cleansing liquid is used up, the nose piece is removed to expose a slot suitable for passing coins and thereby allowing the rocket body to be used as a "piggy bank."

3. Solution to the Problem

Applicant's invention seeks to extend the useful life of a wide variety of relatively small, hand-holdable containers by providing such containers with: (1) esthetically pleasing, animal-simulating, configurations, (2) at least one additional opening that serves to render such containers suitable for a wide variety of "secondary uses" and (3) devices for readily opening the additional opening after the original product originally stored in the container has been used up.

SUMMARY OF THE INVENTION

Hand-holdable containers for products such as after-shave lotion, cologne, shampoo, hair tonic, liquid soap, bubble bath, soap powder, talcum powder, vitamin pills, spices, hard candy, dental floss, beverages, mouthwash and so forth can be given extended useful lives by: (1) providing said containers with a body that simulates at least some of the general configurational and/or anatomical features of an animal such as a dog, cat, pig, cow, goat, lion, horse, bird, fish, whale, insect, etc. so that said containers will be esthetically pleasing as knickknacks, storage containers and/or display holders after the original product contained therein has been used up, (2) providing such containers with a capability to have one or more additional hole(s) suited to some "secondary use", (3) sealing said additional hole(s) while the original product is contained therein and (4) providing means for readily unsealing the additional hole(s) after the original product has been used up.

It should be understood that the containers contemplated in this patent disclosure are intended to "simulate" not only animals that are actually found in nature, but also to simulate: (1) extinct animals (e.g., dinosaurs), (2) mythical animals (e.g., dragons), (3) animals being ridden by humans (e.g., a horse carrying a cowboy, etc.) and (4) "fantastic" animals, such as those having the features of two or more different animal species. In short, this invention contemplates a great deal of "artistic license" in depicting the features of the animal being simulated—to achieve a wide variety of artistic, esthetic, fantasy or comic effects.

Next, it should be noted that, for the purposes of this patent disclosure, the term "hand-holdable" container should be taken to mean those containers capable of containing from about 2 to about 32 fluid ounces. It is even more preferable that the containers of this patent disclosure have volume capacities of from about 3 to about 12 fluid ounces. The original product stored in such containers, be that product a liquid, an aerosol material, a powdered solid, or larger solid pieces such as candy or dental floss, may be contained for the most part in a cavity-containing midsection of the hereindescribed animal-simulating containers. This cavity will, to some degree, extend into the neck and/or head region of the animal being simulated and it may also extend into a leg or base region of the container upon which such a simulated animal may rest.

The original product is dispensed from such containers via a first opening (or first openings) located in the upper neck region of the animal being simulated. Such upper neck region will often be referred to in this patent disclosure as the "neck" of a given animal—even though other terms such as "base of skull" may be somewhat more precise or descriptive. Terminology aside, this neck region is provided with a cap that depicts the simulated animal's head and serves to close the first opening(s) in the neck region and thereby contain the product when it is not being dispensed from said container and—to some degree—it also will "simulate", or "exaggerate", some distinct feature of the animal's head. Thus, the animal's head will be referred to as the "head (cap)" for purposes of this patent disclosure. This head cap may be attached to, and detached from, the neck. It will normally will be mounted on a side-facing, region of the container (e.g., the "left side" of the containers depicted in FIGS. 4 to 13)—as opposed to being mounted on a "top" region of said containers—that is to say a "top" region when the animal being simulated is regarded as standing on its feet or resting on its belly.

In some particularly preferred embodiments of this invention, the head (cap) will have threads adapted for threaded cooperation with threads in the neck of the simulated animal's anatomy. In other preferred embodiments of this invention, the neck is provided with an opening (or openings) having a configuration (e.g., a tapered configuration) suitable for creating a compression fit with a stem (or stems) provided on the underside of the head (cap) that is associated with the container. In still other preferred embodiments of this invention, the head (cap) is provided with a moveable front piece that is connected to a dispensing valve that creates a passage through the head (cap) itself, thereby permitting the user to dispense the stored product without having to actually remove the head (cap) from the container. Indeed, in some particularly preferred embodiments of this invention, such a flow-through head (cap) may be "permanently" mounted to the container by cap locking devices well known to the cap and small container manufacturing arts.

Applicant's simulated animal containers also will be provided with one or more second opening(s), or they may be provided with certain thin surfaces suitable for easily creating such second openings by means hereinafter more fully described. In either case, such second openings are made in sizes suitable for passing relatively small items such as coins, pieces of hard candy, dental floss or powdered materials such as spices, etc., or they may be made suitable for positioning appropriate items such as flower stems, pencils, etc., after the product originally stored in the container has been used up and the container is ready to be converted to its "secondary" use.

Such a second opening may, for example, take the form of an upward facing, horizontally extending, slot-like, opening in the "spinal" region of the animal being simulated a la the coin slot in a "piggy bank". Such second opening(s) may, however, have a wide variety of other geometrical shapes, e.g., round or rectangular holes. In one particularly preferred embodiment of this invention, the second opening will be provided in the form of an externally threaded second neck having a bore-like passage leading to the interior cavity of the container. In another particularly preferred embodiments, especially in those cases where the container is made of a plastic material, the second "opening" may take the form of a partially completed hole having a core region of decreased thickness that can be readily removed e.g., by being "punched in" or "cut out" with a sharp instrument such as the point of a knife in order to create a "true" hole that is capable of admitting a "secondary" item such as a coin into the container when it is time to convert said container to its secondary use. Such a second hole also might take the form of a small hole in the animal's foot through which a product having a relatively small cross sectional diameter (e.g., dental floss) is dispensed.

Such second opening(s) also may be located at various other places on the anatomy of the simulated animal e.g., in its head, ribs, belly, etc. In still other embodiments of this invention, multiple second openings suitable for holding a group of similarly shaped items such as pencils or flower stems will be provided in these containers. These second openings also may be large enough to allow finger accessibility to the inside regions of the container, e.g., a second opening may be large enough to allow human fingers to pick up pieces of hard candy stored in said container. Such second openings also may take the form of a "hinged" trap door-like opening in, say, the simulated animal's belly region.

The hereindescribed animal-configured containers of this patent disclosure also may contain a third opening, and especially a third opening having a configuration different from the second opening. Such third openings may be particularly suitable for receiving nozzles and similar dispensing devices that are frequently used to dispense liquids from automated, bottle-filling equipment. For example, such third openings may be a round hole large enough to receive a nozzle that is used to automatically dispense a liquid, such as after-shave lotion, into such containers. These third openings also may take the form of a small hole through which a string-like product such as dental floss, thread or string is dispensed.

In some embodiments of this invention, this third opening can be separate and distinct from the second opening. Such "third" opening(s) may, however, also be combined with the second opening(s) in ways hereafter more fully described. In the case of liquid or powdered original products, a slot-like second opening could also be used to load such products into the container; hence, no third opening would be needed. Larger, solid, items such as pieces of hard candy, vitamin pills, etc., would, however, normally require a second or third hole larger than a slot capable of admitting a coin in an edge-wise manner. Here again, a trap door-like third opening in the animal's belly region also could be used for such purposes. Larger, solid products (such as pieces of hard candy) also could be loaded into the container as original products via the first opening from which they are dispensed.

The second and/or third opening(s) will normally be filled with, or covered by, appropriately sized and configured plugs or caps while the container is being used to store and dispense the product originally contained therein. By way of example, a threaded plug may be associated with a threaded second (and/or third) opening. Similarly, a threaded second neck may be covered by an appropriately threaded cap. By way of a further example, an unthreaded second (and/or third) opening may be filled with a compression-fitting plug. The "compressibility" of such a compression-fitting plug may be achieved by simply making it in a suitable size and geometry to fill the second (or third) opening, and making it out of a slightly compressible plastic material such as polyurethane and compression-fitting it into a given second (and/or third) opening after the container has been filled with its original product. Such plugs also may be provided with tabs—and most preferably "finger-grippable" or "plier-grippable" tabs—so that such plugs can be twisted from, or pulled from, the second (and third) opening(s) when the product originally stored in the container has been used up. In those instances in which the second opening is large enough to accommodate human fingers reaching into the container's cavity, such a second opening may be sealed with a plug that is perhaps better described as a "lid." Such lids also may be provided with a tab or handle for use in gripping and positioning the lid back upon the second opening when said container is being used to store certain "secondary" products such as pieces of candy.

As previously noted, the "plug(s)" that fill these second (or third openings) while the original product is stored therein also may exist in the form of a layer of the material from which the container wall in the area immediately surrounding the second (or third) opening is made— especially when that material is a relatively soft thermoformable plastic. Such a layer will preferably be thinner than the container wall in the area immediately surrounding this thinner layer. Such a thinner layer, in effect, will form what might be called a "latent" second opening that can be converted into a "true" second opening (one that allows passage of an object) by removing said thinner layer, e.g., by punching in and/or cutting out the thinner layer of material after the original product has been used up. Again, such thinner layers can be easily removed when the container is made of relatively "soft" plastic materials well known to the plastic bottle molding arts. Those skilled in the plastic molding arts will appreciate that the mold configuration can be used to create the thinner layer (relative to the thickness of the surrounding region of the container wall) in such a "latent" second (or third) hole.

Thus, in their original product storing and dispensing forms, the containers of this patent disclosure generally will be comprised of a main body region (that may include a simulated animal's head and its base) having a cavity for storing the original product, the original product itself, at least one sealed second opening for containing the original product therein when said product is a liquid or powder (this would not be necessary if the product were certain solids (e.g., dental floss)), a neck region that has at least one first opening for dispensing the product, and a head (cap) that covers said first opening. The first opening is in fluid communication with the cavity in the container where the original product is stored. The first opening (or first openings) should be appropriately sized to pass the product originally stored therein. For example, if the container is originally used to store and dispense vitamin pills, the container's first opening will be considerably larger than if the container is originally used to store, and "sparingly" dispense, a liquid product such as after-shave lotion. Auxiliary dispensing adapters, hereinafter more fully described, also may be placed in the simulated animal's neck region to give the hereindescribed containers wider versatilities with respect to their product dispensing capabilities.

The exterior of the midsection of the animal's body may be further provided with labels that serve to impart information, advertisements, warnings, etc., concerning the original product being stored in the container. Finally, the act of twisting off, or otherwise moving or operating some part of the head (cap), or a dispensing valve of a flow-through head cap, can be used to initiate an electrical signal to cause sound-generating devices associated with the overall container (e.g., sound-emitting devices placed in the body or in the head cap of said container) to generate a sound such as, for example, the sound made by the animal being simulated. For example, a pig-shaped container might be programmed, by computer chip devices that are well known to the microelectronic arts, to emit an "oink, oink" sound as the head (cap) is being removed from a pig-shaped container.

The container body, head (cap), second cap (if any) and plug(s) each can be made from a variety of materials such as various thermoplastic polymers (polystyrene, polyethylene, polypropylene, etc.) glass, ceramic materials, etc. using a wide variety of known manufacturing procedures (e.g., injection molding, blow molding, glass blowing, etc.). If a polymer material is employed, it also should be capable of withstanding chemical attack by the product originally stored therein (e.g., by an alcohol-based, after-shave lotion). It also is contemplated that applicant's containers can be made of a flexible, hand-squeezable, plastic materials to aid in dispensing a liquid product such as after-shave lotion, liquid soap or a viscous shampoo from such containers. When compression-fitting plug(s) is (are) employed, it (they) will preferably be made from a thermoplastic polymer (e.g., polyurethane) having a relatively high elastic modulus, that is to say, higher than the elastic modulus of the material from which the container body is made so that the plug will hold a tight compression fit with the hole in said container that the plug fills. Such a plug should likewise be capable of withstanding chemical attack by the product being stored in the container.

BRIEF DESCRIPTION OF THE DRAWINGS

FIG. 1 is a perspective view of a pig-shaped container made according to the teachings of this patent disclosure and having a pig's head-simulating cap.

FIG. 2 is a frontal view of an alternative pig-shaped container.

FIG. 3 depicts the pig-shaped container shown in FIG. 1 in an "upright" position made possible by virtue of the fact that the rear end of the pig-shaped container is provided with a flat, base-forming surface.

FIG. 4 depicts, in cross-section, a pig-shaped container provided with an externally threaded neck region for receiving an internally threaded head (cap).

FIG. 4(a) depicts, in cross-section, a head (cap) used to cover a flow-through cap mounted to the neck region of the pig.

FIG. 5 depicts, in partial cut-away, a pig-shaped container that is provided with an internally threaded first opening in its neck region that is capable of receiving an externally threaded stem mounted on a head (cap) to be associated with this container.

FIG. 6 depicts a pig-shaped container that is provided with a coin slot in its rib region. It is also shown provided with a tapered first opening in the pig's neck that is adapted to form a compression fit with a similarly tapered stem on the inside of a head (cap) to be associated with this container.

FIG. 7 depicts a pig-shaped container that is provided with a head (cap) having a flow-through valve in the nose region of the head (cap). This flow-through valve can be pulled forward to allow flow of product through the head (cap) without having to remove said head (cap) from the container. The body region of the container shown in FIG. 7 also is shown provided with several "second" openings that are each occupied by a pencil or pen.

FIG. 9 also depicts an externally threaded second opening.

DETAILED DESCRIPTION OF THE INVENTION

Figure 8:
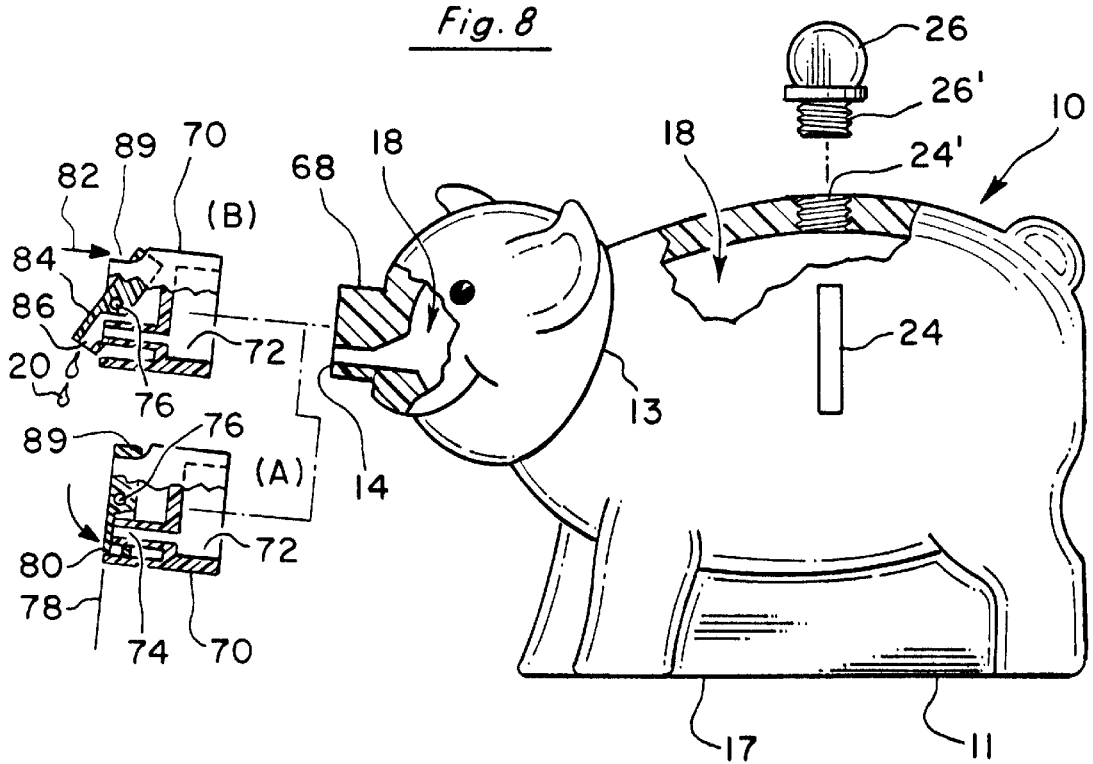
FIG. 8 depicts a pig-shaped, container. The plug for the second opening in this container is shown having a threaded stem for threaded cooperation with a threaded second opening. This container also is provided with a head (cap) having a pivotally mounted valve in its nose region that can be pivoted to expose its dispenser opening and thereby allowing flow of a liquid or powdered product through the head (cap) without having to actually remove said head (cap) from the container.

FIG. 1 depicts a hand-holdable container 10 having, for purposes of illustrating an animal-simulating container suitable for the practice of this invention, the shape and general anatomical features of a four legged animal, to wit, a pig. Again, it should be appreciated that the shape of any number of other natural animals (or mythical animals or fantasy animals) having at least some of the features or attributes of an animal could serve as a model for the shape of applicant's containers. Thus, such containers could, for example, resemble a dog, cat, cow, goat, tiger, bear, bird, lion, kangaroo, porcupine, horse, sheep, insect, fish, dolphin, alligator, dragon, satyr, etc., in any physical position (e.g., standing, running, sitting, flying, swimming), without departing from the scope and spirit of this patent disclosure. In this regard, the only requirement will be that the animal being simulated have at least some recognizable features that give the container an ability to simulate, to some degree, an animal or fantasy animal. Such animals or fantasy animals also may be depicted as being "ridden" e.g., a cowboy riding a horse.

Be such animal configurations as they may, FIG. 1 specifically shows how a head (cap) 12 may be used to "simulate" a pig's head. The head (cap) 12 separates from the neck along head/neck rim line 13. This container 10 also is depicted in a "secondary use" role wherein a coin 13 is about to be inserted into a slot-like opening 24 in the "spinal" region of the midsection of the pig-simulating container 10. FIG. 1 also is intended to illustrate that, even though the animal-simulating configurations of this patent disclosure may well include separate and distinct legs, in some preferred embodiments, applicant's containers will have a unified base region 11 that comprises a single piece (rather than separate and distinct legs). Such a unified base may, however, be given the general outline and outward appearance of legs A, B, C and D, so as to give the visual impression of being separate and distinct legs. The product-containing cavity also may extend well into this base region 11 for added storage capacity. This same effect can likewise be used in simulation of animals having two legs (e.g., a bird or an ape). An animal such as a whale, having no legs, would simply be mounted on a base that blends into that animal's belly region in the manner generally illustrated in FIG. 13. The bottom of base 11 should most preferably present a substantially flat surface 17 upon which the container can be set in a generally horizontal orientation in order to present the animal in a "normal" standing, sitting, lying or flying position.

FIG. 2 is a frontal view of another pig-shaped container. It further illustrates how the head (cap) 12 may be made to better simulate the snout region of a pig. FIG. 2 also illustrates an embodiment of this invention wherein the bottom of the container is in fact provided with separate and distinct legs (e.g., as seen in this view, front legs A and B) rather than being provided with a unified, monolithic, base such as that depicted in FIG. 1. Such legs should also form a stable base 17 upon which to set the container in a generally horizontal orientation such as that depicted in FIGS. 1 and 2. FIG. 2 suggests the preferred, "counterclockwise", direction of turning 19, that serves to remove the head (cap) 12 from the container 10 when the head (cap) is in fact a "removable" head (cap). Conversely, a "clockwise" turning is preferred to mount such a threaded head (cap) 12 on the containers of this patent disclosure.

FIG. 3 depicts the container 10 sitting in an, "unnatural", legs extended, rear end-sitting, position made possible by the fact that the rear end of the pig-simulating container has been provided with one or more flat regions (e.g., 15 and 15') that can serve as a stable base 19 upon which to stand the container in a vertical or "upright" orientation. This is a convenient feature for storing the containers of this patent disclosure in confined places such as upon the shelves of medicine cabinets. FIG. 3 is shown in partial cut away to illustrate another embodiment of this invention wherein the initial product being stored is a string-like product 2 such as dental floss, thread, package tying string and the like. Such a string-like product 2 may be dispensed through a second hole 1' in the simulated animal's foot. The nose region also may be provided with a string cutting device 3 such as those commonly used to cut dental floss to convenient lengths. Such a string-like product 2 can be wound on a spool 4 having a hole 5 which is mounted on a mounting post 6 so that the spool 4 may rotate on the mounting post 6 and thereby dispense the string-like product 2 as it is pulled from a dispensing hole. FIG. 3 also illustrates how the internal cavity of the containers of this patent disclosure may be compartmentalized into two or more separate and distinct, and even water tight, compartments 18 and 18' by means of a compartment wall 8. Thus the containers of this patent disclosure may contain more than one original product. By way of example, the lower compartment could contain dental floss that is dispensed from a second hole 1' in the pig's foot, while the upper compartment could contain an after-shave lotion product 20' that is dispensed from a first hole 1 in the pig's neck region after the head (cap) 12 has been removed from the container 10.

FIG. 4 depicts a cut-away side view of an "uncapped" rendition of the hand-holdable container 10 shown in FIG. 1. The head (cap) 12 is located on a side (the left, or front "face", side 23) of the animal-shaped container rather than upon a top side of said container (e.g., rather than upon the pig's "spine") when the pig is regarded as standing in a "natural", horizontal orientation upon its simulated four legs (i.e., upon the base 11 shown in FIG. 1). The "inner" (that is "uncapped") neck region 14 of the pig is shown provided with external threads 36 for removably attaching an internally threaded head (cap) 12 to said neck region 14 of the pig-shaped container 10. The neck region 14 has at least one first opening 16 that is in fluid communication with a cavity 18 in the container 10. Again, this first opening 16 will generally extend from the simulated animal's mid-body region and through the neck region 14 as generally suggested in FIG. 4.

The first opening 16 serves to dispense an original product 20. In use, a liquid or powdered original product 20 will normally be dispensed from the first opening(s) 16 by tilting, shaking and/or squeezing the container 10 by hand. The center line 39 of the head (cap) and first hole is shown in FIG. 4 as being tilted at an "upward" angle theta $\theta$ relative to the "horizontal" base 17 of the container. This center line 39 could also be parallel to the horizontal plane 17 of the base, or it could be tilted "downward" with respect to the horizontal plane 17 of the base 11 (in effect this would cause the pig depicted in FIG. 4 to appear as though it were looking downward, toward "the ground"). It is preferred, however, that this center line 39 not be truly vertical—that is say normal to the horizontal plane 17 of the base 11 when the pig is in a natural standing position such as that depicted in FIG. 4. This preference for a non-vertical center line for the head (cap) and first opening implies that the head (cap) and first opening, preferably, are not located in a "top" region of horizontally oriented animal e.g., in the top of its spinal region, since such a positioning would produce some necessity to "invert" the horizontally oriented container in order to dispense the product contained therein. Given the horizontal orientation of the container and the hand/wrist movements needed to accomplish an inversion of such containers, once they are initially gripped by a user's hand, may be somewhat awkward and, for some users, may even require the use of two hands. Thus, it is preferred that the head (cap) for many of the hereindescribed containers will extend from a side of the simulated animal (e.g., the left or face side 23 as depicted in FIG. 4) rather than extend from a top surface of the container in the manner of most prior art, hand-holdable, "upright standing" containers such as beverage bottles, shaving lotion bottles and the like having "vertical" head (cap)/bottle opening center lines. This head (cap) location should be regarded as a strong preference rather than an absolute prohibition since some configurations (e.g., a wolf in a sitting position with its head thrown back to howl) may place the head (cap) centerline in a vertical or nearly vertical orientation. Be this preference for a horizontal orientation for sitting these containers on their base 17 as it may, the "rear" 19 of the containers of this patent disclosure will, most preferably, be capable of forming a stable base (e.g., on rear base portions 15 and 15') upon which the containers of this patent disclosure can be set in an "upright", albeit "unnatural appearing", orientation such as that suggested in FIG. 3. This feature greatly aids in storing the hereindescribed containers in "cramped quarters" such as the shelves of medicine cabinets.

The midsection of the pig-shaped container 10 of FIG. 4 is shown provided with a second opening 24 for receiving objects such as coins in the manner of a "piggy bank"—after the product 20 that was originally stored in the container 10 has been used up. This midsection also is a preferred location for larger second (and third) openings e.g., larger than the string product dispensing hole 1' shown in FIG. 3. When the container 10 is being used as a container for a liquid or powdered original product 20, the second opening 24 will be sealed tightly shut. Again, this can be accomplished in several ways. For example, a plug 26 can occupy the second opening 24; or the second opening can be made with a thin covering 25 over it by virtue of the way the container is originally molded. Those plugs that are "true", insertable and removable, plugs may be associated with the container in several ways including a "compression fit" of a plug 26 in a second opening 24 as suggested in FIG. 4. Such plug(s) 26 is (are), most preferably, also provided with at least one finger-grippable, tab 28 provided for pulling a plug 26 from a second opening 24 when the time comes to remove said plug(s) 26 from the container 10.

FIG. 4 also illustrates how in another preferred embodiment of this invention, any given second "opening" 24 may be covered with a thin layer 25 of the material from which the container 10 is made (e.g., a plastic material). This construction feature creates what may be termed a "latent" hole that may be converted into a "true" hole—that is, a hole capable of passing a solid object—by simply removing, e.g., "punching in" or "cutting out" this thin layer 25 with an appropriate hand tool such as the point of a knife when the time comes to convert the container to a secondary use. FIG. 4 also shows a highly preferred embodiment of this feature wherein the thickness of this thin layer 25 is less than the thickness of the container wall in the area immediately surrounding this core or latent hole. Thus, for the purposes of this patent disclosure these latent holes, along with the thin layer of material that covers them, should be regarded as falling within the term(s) "second opening" or "third opening".

In yet another preferred embodiment of this invention, the second opening 24 may include a third, hole-like, opening 29, such as those respectively depicted in FIGS. 5 and 6. Such third openings will preferably have a size and/or geometry different from the second opening. In such cases where the second and third holes are so combined, the third opening preferably will have a diameter greater than the thickness of a coin so that the third opening can be conveniently used to fill the container 10 with solid products such as pills. Preferably, the second (and, if need be, third) opening(s) will be in the "spinal region" of the midsection of these containers. This midsection generally will, for the most part, be located in the mid-torso region of the simulated animal's body, e.g., roughly between lines 30 and 32 on the simulated pig of FIG. 4, i.e., in the area generally indicated by the span of item lead line 34. Such second opening may, however, also be in the head or neck or foot—especially when the animal is depicted in a sitting position.

Again, the means for attaching the head (cap) 12 to the neck of the simulated animal's anatomy may vary in ways well known to the bottle and cap manufacturing arts. For example, FIG. 4 illustrates a pig-shaped container 10 having a post 35 that has been provided with an external thread system 36 for receiving an internally threaded hole 38 of a head (cap) 12 to be associated with the pig-shaped container shown in FIG. 4. This head (cap) 12 is shown in cross section—and detached from post 35—in order to better illustrate a thread system that is especially well suited to the practice of this invention. Directional arrow 19 depicts the preferred, counterclockwise, direction for twisting the head (cap) 12 in order to remove it from the container 10. Hence, the head (cap) 12 shown in FIG. 4 can be readily reattached to the pig's neck region 14 by twisting said head (cap) 12 on to post 35 in a clockwise direction.

FIG. 4(A) depicts another embodiment of this invention wherein the neck region 14' is provided with a first external thread system 36' for threaded engagement with internal threads on a flow through cap 52'. The flow through cap 52' has a dispensing head 53' that can be pulled in an upward direction by the user's finger tips. When the dispensing head is pulled up, a hole 55' in the dispensing head 53' is opened to allow product flow through passageway 16' and the flow through cap 52'. Conversely, when the dispensing head 53' is pushed down, a post-like element 57' occupies the dispensing hole 55' and thereby serves as a valve that shuts off flow of product through flow through cap 52'. The pig's head (cap) 12' is hollow and thereby serves as a cover for the flow through cap 52'. The pig's head (cap) 12' is provided with internal threads 38' for threaded engagement with a second thread system 37' of the neck region 14'.

FIG. 5 depicts a container wherein a pig's neck region 14 has been provided with a first opening 40 that leads to cavity 18. This first opening 40 is shown provided with internal threads 41 for threaded cooperation with an externally threaded stem 42 on a head (cap) 12 to be associated with the pig-shaped container 10 of FIG. 5. A plug 26 having an enlarged circular center region 27 for occupying a suitably configured hole 29, and preferably one having a diameter greater than the width of slot-like second opening 24 is shown located near the center of the slot-like second opening 24. This plug 26 also is shown provided with finger-grippable tabs 28 to facilitate removal of said plug 26 from the second opening 24. This container 10 also is shown provided with a label 44 that can be used to give information about the product, make advertisements, make warnings and so forth.

FIG. 6 illustrates a pig-shaped container 10 having a somewhat conically-shaped hole 46 in its neck region 14 for receiving a conically shaped post 48 of head (cap) 12 in a "compression type fit" that does not involve a thread system. The conical nature of these two elements has been exaggerated somewhat in FIG. 6 in order to better illustrate these conical configurations. In another preferred embodiment of this invention, the post 48 will be further provided with a stop rim 48' that serves—when the head (cap) 12 is mounted to the container 10—to prevent the rear of the head (cap) 12 from completely abutting against the front 49 of the neck region 14. This in turn serves to position a portion of the head (cap) 12 slightly away from the front 49 of the neck region 14. This arrangement facilitates finger tip or fingernail gripping the head (cap) 12 in order to pull it out of hole 46. The second opening 24 in FIG. 6 is shown with a third hole 29 suited to receiving flow from a dispensing nozzle 47 such as those commonly used in automated bottle-filling equipment. The container 10 is shown in FIG. 6 with a second, slot-like, additional opening 24' that is filled with a plug 26 having tabs 28 for removing said plug 26. A third opening having a size and geometry different from that of second opening is shown in the pig's belly region being occupied by another type of plug 24".

FIG. 7 illustrates a pig-shaped container 10 shown with a detachable head (cap) 52 that is threadedly attached to said container 10. The head 12 also is provided with a passageway 16 through which product can flow through the head to a flow through head (cap) 52. The nose region 21 of the detachable head (cap) 52 has been provided with an externally threaded post 50 for threaded cooperation with a threaded hole 51 of a "flow-through" type head (cap) 52. This flow-through head (cap) 52 can be threaded on to post 50—but it does not have to be removed from post 50 in order to dispense product 20 from the container 10. Indeed, the flow-through head caps that may be employed on the containers of this patent disclosure may be "permanently" attached to such containers by bottle cap locking devices well known to the cap and bottle manufacturing arts. Thus, these flow-through valve-containing head caps can be threaded on to, and then locked on to, such containers. These flow-through head caps need not even be provided with threads if they are to be "permanently" mounted to the container. For example, such flow-through head caps may be mounted to the nose region of a simulated animal by other well known mechanical devices, e.g., by so-called "bayonet locking devices" that usually operate by forcing a nub on one component into alignment with a receiving groove having a nub-receiving indentation on another component and then rotating one component with respect to the other until the nub enters the nub-receiving indentation. Regardless of the mode by which they are attached to the container, however, such flow through head caps are especially useful when the original product 20 being dispensed through them is a liquid or freely flowing powder.

Those skilled in this art will appreciate that there are several different kinds valving systems for the flow through head caps that may be employed in the practice of this invention. For example, FIG. 7 illustrates such a flow-through capability provided by a head (cap) 52 having a dispensing valve 50' that is pulled to a "forward" position 54 in order to open dispensing hole 55 of dispensing valve 50', and thereby allowing a liquid product such as after-shave lotion or liquid soap to flow through the head (cap) 52 while the head (cap) remains mounted on the container 10. Flow-through head caps having product dispensing valves of this kind can be further provided with a ridge 53 that can be gripped by the user's finger tips in order to pull a dispensing nozzle 53' of dispensing valve 52 to a forward position 54 and thereby creating a passage through said head (cap) 52. When the dispensing valve 50' is forced back toward the container to a rearward position 56, the dispensing hole 55 is occupied by post 57; and hence, product 20 will no longer be able to pass through the head (cap) 52. Finally, FIG. 7 illustrates a secondary "display" embodiment of this invention wherein several second openings 24 are each shown holding a respective pencil or pen 58 for secondary "display" and utility purposes.

FIG. 8 depicts a container 10 having a plug 26 provided with threads 26' for threaded cooperation with a threaded second opening 24'. Another second opening 24 in the form of a coin slot 24 is shown in the rib region of the pig-shaped container 10. The head (cap) 12 is shown attached to the container 10, but the head and neck of this pig-shaped container separate along rim line 13. The nose of this pig is shown provided with threads 68 in order to attach and detach a threaded flow-through cap 70 to the container 10. That is to say that external threads 68 on the container cooperate with the internal threads 72 of the flow-through cap. This particular head (cap) 12 also illustrates another type of flow-through valve mechanism. For purposes of such illustration, it is depicted in two distinct operating positions that are respectively illustrated in details (A) and (B). In detail (A), a flow-through valve 74 in the nose region of the head cap is shown mounted on a pivot 76. This flow-through valve 74 is depicted in its closed position wherein it is flush with the plane 78 of the nose region of flow-through cap 70. It is moved to this closed position by pushing in on its lower edge 80 as suggested by the directional arrow 81 shown in FIG. A. Detail B shows the flow-through valve 74 in its open position. This is accomplished by pushing inward at the upper edge 82 of the pivotally-mounted flow-through valve 74 and thereby causing said valve's lower region 84 to project outward. This outward projection in turn exposes the valve's fluid dispensing hole 86 so that product 20 may be dispensed from said hole 86. An indentation 89 in the nose region of cap 70 can be provided to facilitate finger tip pushing of the flow-through valve 74 to the open, product-dispensing, position shown in detail B.

Figure 9:
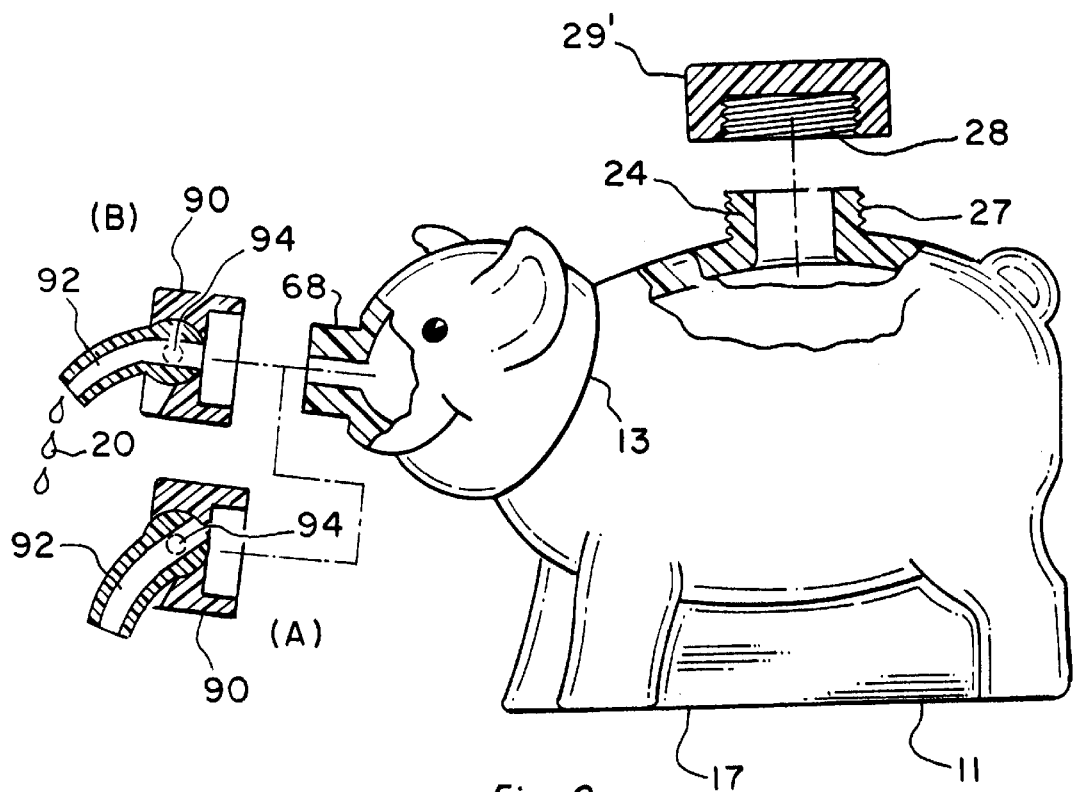
FIG. 9 depicts a pig-shaped container having a spout-like valve that swings out of the front face of the head (cap) to allow flow of product through the head (cap) without having to actually remove said head (cap) from the container.

FIG. 9 depicts a pig-shaped container 10 having a cap 90 that has yet another kind of flow-through valve 92. It is mounted on a pivot 94 so that it can be pulled from the closed position depicted in detail A to the open position depicted in detail B in order to dispense product 20. This container 10 is shown provided with a second hole 24 having external threads 27 that cooperate with internal threads 28 of a cap 29'.

Figure 10:
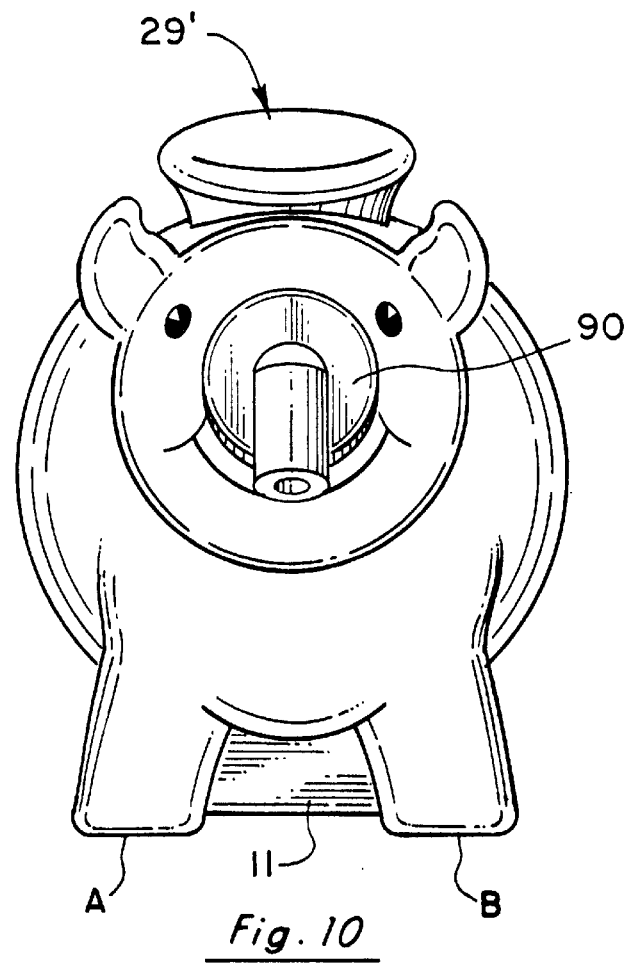
FIG. 10 depicts the front view of the container of FIG. 9.

FIG. 10 depicts the pig-shaped container of FIG. 9 in a front view that illustrates that the base 11 extends between legs A and B.

Figure 11:
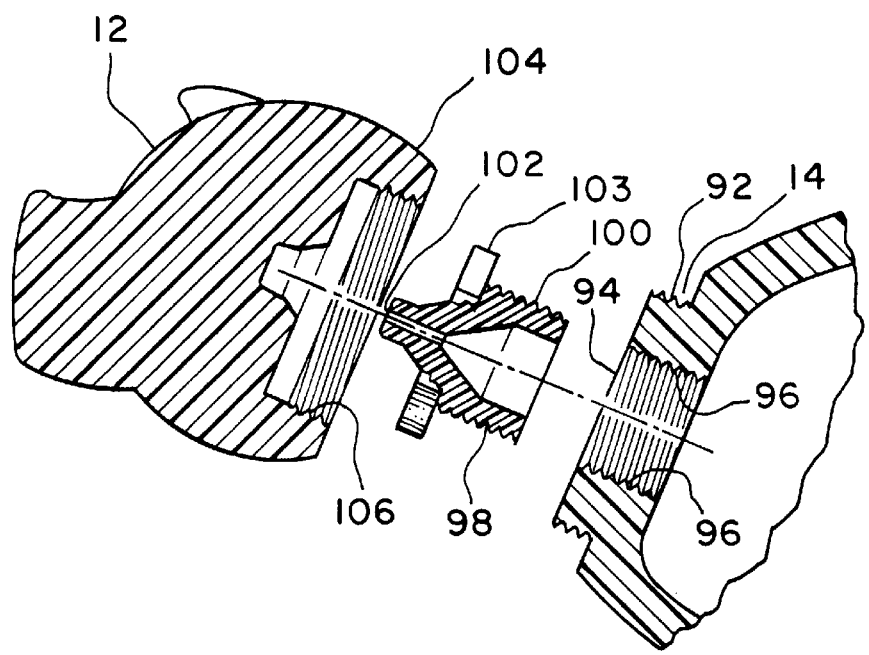
FIG. 11 depicts the use of an auxiliary adapter that facilitates dispensing a liquid-type original product and that, when removed, also facilitates removing solid secondary items, such as stored coins, from the container.

FIG. 11 depicts the head and neck region of a pig-shaped container having external threads 92 in its neck region. The neck region is also shown provided with a relatively large hole 94 (relative to hole 102 of adapter 98) that is provided with internal threads 96. This relatively large hole 94 can be fitted with a dispensing adapter 98. This dispensing adapter 98 is provided with external threads 100 for threaded cooperation with internal threads 96 of the relatively large hole 94. The adapter 98 also could be provided with a tapered smooth bore tube (rather than threads 100) and simply compression fitted into a large hole 94 that, likewise, would have no threads. Be that as it may, the adapter 98 shown in FIG. 4 is shown provided with a small hole 102 adapted to "sparingly" dispense a liquid product such as after-shave lotion. This adapter 98 also may be provided with a raised surface 103 (e.g., in the form of a hexagonal nut) for gripping and twisting the adapter 98 to remove it from hole 94. Thus, after a liquid product has been used up, such an adapter 98 can be removed from large hole 94 so that relatively large solid "secondary" items, such as coins, can be thereafter readily removed from said container—via the hole 94 left open when the adapter 98 is removed from the container. The adapter 98, as well as threads 92 on neck 14, can be covered by a head (cap) 104 having internal threads 106 that cooperate with, and cover, external threads 92 on the pig's neck region 14.

Figure 12:
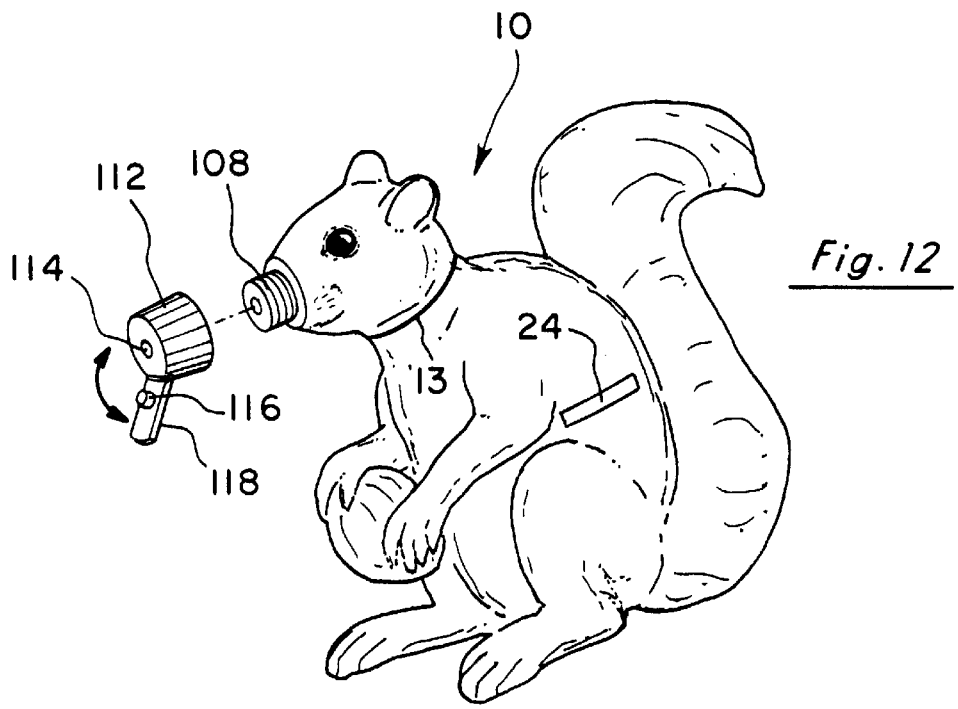
FIG. 12 depicts a container having the general appearance of a sitting squirrel and having a threaded neck (not shown) for receiving a threaded head (cap). The head (cap) is further provided with a hinged front snout piece that serves as a liquid product dispensing valve.

FIG. 12 depicts a squirrel-shaped container 10 wherein the squirrel is in a sitting position. The squirrel's neck region depicts rim line 13 where the squirrel's head detaches from its neck. The squirrel's nose region is shown provided with a threaded post 108 for threaded cooperation with an internally threaded hole (not shown) of a nose-like cap 112. The nose-like cap 112 is shown provided with a flow-through hole 114 that is filled with a stopper nub valve 116 mounted on a hinged front face tab 118 of said cap 112.

Figure 13:
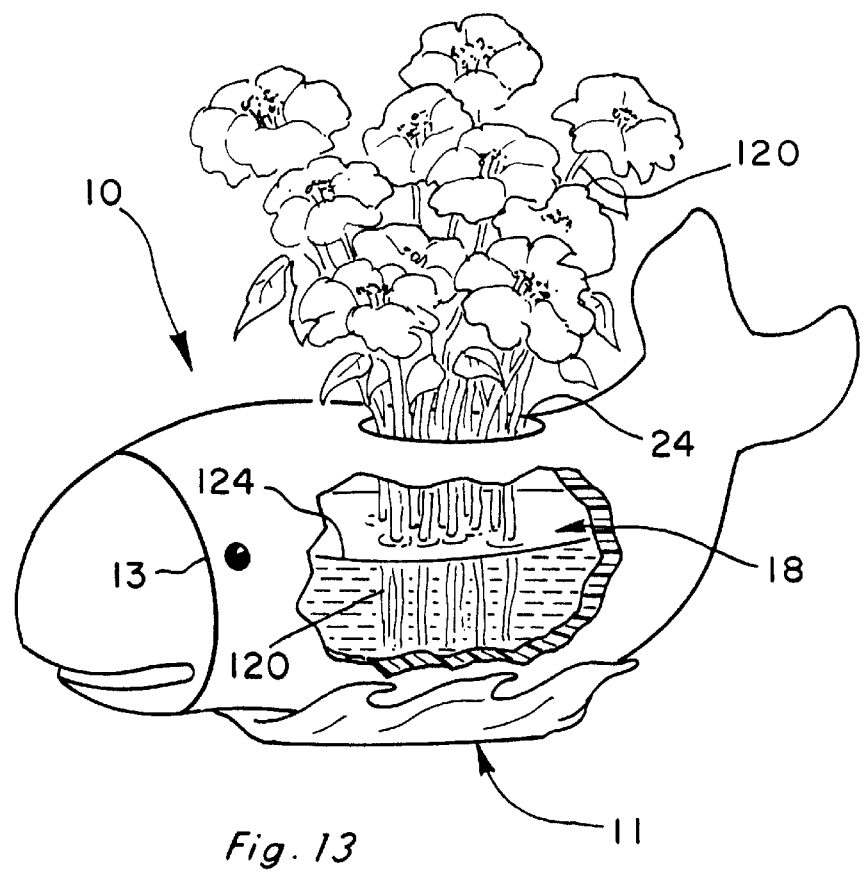
FIG. 13 depicts a whale-shaped figure having a base that blends into the belly region of said whale. The whale-shaped container is shown provided with a second opening that is shown holding flower stems that extend to the inner cavity of this container so that it can carry out the function of a flower vase.

FIG. 13 depicts a whale-shaped container 10 whose belly region blends into its flat base 11. The whale's head detaches from its neck along rim line 13. The second opening 24 of this container is shown holding flower stems 120. The cavity 18 is shown provided with water 124 into which the stems 120 extend so that the container 10 can serve as a flower vase.

It should be appreciated that only a few of the many possible animal, or fantasy animal, configurations that might be employed in the practice of this invention have been illustrated in this patent disclosure. Consequently, the scope of this invention should be limited only by the scope of the patent claims that follow.

We claim:

1. A hand-holdable container, said container comprising a body that simulates at least some of the anatomical features of an animal and wherein a neck region of said body has a first opening for dispensing an original product from the container and threads for attaching a head to said neck region, and wherein said container is further provided with at least one sealed second opening that is in the form of a slot capable of passing a coin and wherein said second opening is provided with a plug that is compression fitted in said second opening so that said plug can be removed when the original product has been used up and thereby rendering said container suitable for a secondary use.

2. The container of claim 1 that further comprises a head having internal threads capable of being threadedly attached to, and detached from, threads on said neck region.

3. The container of claim 1 wherein the threads for attaching the head to said neck constitute a thread system that is so constructed that turning the head in a counter-clockwise direction with respect to a front view of said animal's nose region will remove the head from the container.

4. The container of claim 1 wherein said container is provided with a dispensing adapter.

5. The container of claim 1 that further comprises a stable base-forming rear end suitable for setting the container in an upright position.

6. The container of claim 1 wherein said container is made of a thermoformable plastic material.

7. The container of claim 1 wherein said container is made of a flexible, thermoformable, plastic material capable of being squeezed by pressure supplied by a user's hand.

* * * * *